(12) United States Patent
Chang et al.

(10) Patent No.: US 7,851,504 B2
(45) Date of Patent: Dec. 14, 2010

(54) ENHANCED BIMATOPROST OPHTHALMIC SOLUTION

(75) Inventors: Chin-Ming Chang, Tustin, CA (US); James N. Chang, Newport Beach, CA (US); Rhett M. Schiffman, Laguna Beach, CA (US); R. Scott Jordan, Trabuco Canyon, CA (US); Joan-En Chang-Lin, Tustin, CA (US)

(73) Assignee: Allergan, Inc., Irvine, CA (US)

( * ) Notice: Subject to any disclaimer, the term of this patent is extended or adjusted under 35 U.S.C. 154(b) by 819 days.

(21) Appl. No.: 11/083,261

(22) Filed: Mar. 16, 2005

(65) Prior Publication Data

US 2006/0211770 A1 Sep. 21, 2006

(51) Int. Cl.
*A61K 31/19* (2006.01)
*A61K 31/215* (2006.01)
(52) U.S. Cl. ...................... 514/530; 514/573
(58) Field of Classification Search .......... 514/530, 514/575
See application file for complete search history.

(56) References Cited

U.S. PATENT DOCUMENTS

| | | | |
|---|---|---|---|
| 4,128,577 A | 12/1978 | Nelson | |
| 4,543,353 A | 9/1985 | Faustini | |
| 4,812,457 A | 3/1989 | Narumiya | |
| 5,474,979 A | 12/1995 | Ding et al. | 243/279 |
| 6,596,765 B2 | 7/2003 | Ueno | 514/530 |
| 6,646,001 B2 | 11/2003 | Hellberg et al. | 514/530 |
| 6,743,439 B1 | 6/2004 | Castillo et al. | |
| 2005/0004074 A1 | 1/2005 | Lyons et al. | |

FOREIGN PATENT DOCUMENTS

| | | |
|---|---|---|
| CA | 2498233 | 3/2004 |
| EP | 0098141 | 11/1984 |
| FR | 2239458 | 7/1973 |
| JP | S49-69636 | 7/1974 |
| JP | S62215537 | 9/1987 |
| WO | WO2004/133119 | 2/2004 |

OTHER PUBLICATIONS

Bito, L.Z. & Baroody, R.A., The Ocular Pharmacokinetics of Eicosanoids and Their Derivatives . . . , 44 Exp. Eye Res. 217-26 (1987).
Pfeiffer, N., New Development in Glaucoma Drug Therapy, 89 Ophthalmologe W1-W13 (1992).
Schumer, Robert A., MD, PhD & Podos, Steven M.,MD, Medical Treatment of Glaucoma, 2 Ophthalmology 140-50 (1991).
Woodford Roger, PhD & Barry, Brian W., PhD, Penetration Enhancers and the Percutaneous Absorption of Drugs: An Update, 5(3) J. Toxicology.—Cut. & Ocular Toxicology 167-77.
Faulkner, R., Aqueous Humor Concentrations of Bimatoprost Free Acid, Bimatoprost and Travoprost . . . , 26 Journal of Ocular Pharmacology and Therapeutics, 147-156 (2010).
Camras, Carl B., Detection of the Free Acid of Bimatoprost in Aqueous Humor Samples from Human Eyes . . . , 111 Ophthamology 2193-2198 (2004).
Cantor, Louis B., Levels of bimatoprost acid in the aqueous humor after bimatoprost treatment . . . , 91 Br J Ophthalmol 629-632 (2007).
Noecker, Robert J., *Corneal and Conjunctival Changes Caused by Commonly Used Glaucoma Medications*, Cornea, vol. 23, No. 5, 490-496 (Jul. 2004).
Kaur, I.P., *Penetration enhancers and ocular bioadhesives: Two new avenues for ophthalmic drug delivery*, Drug Development and Industrial Pharmacy, 28(4), 353-369 (2002).

*Primary Examiner*—Zohreh A Fay
(74) *Attorney, Agent, or Firm*—John E. Wurst; Kevin J. Forrestal; Doina G. Ene

(57) ABSTRACT

A composition comprising from 0.005% to 0.02% bimatoprost by weight and from 100 ppm to 250 ppm benzalkonium chloride, wherein said composition is an aqueous liquid which is formulated for ophthalmic administration is disclosed herein.

A method which is useful in treating glaucoma or ocular hypertension related thereto is also disclosed herein.

3 Claims, 2 Drawing Sheets

ENHANCED BIMATOPROST OPHTHALMIC SOLUTION

FIELD OF THE INVENTION

This invention relates to pharmaceutical compositions comprising bimatoprost.

BACKGROUND OF THE INVENTION

Description of Related Art

Bimatoprost, shown below, is a prostamide marketed commercially for the treatment of glaucoma and ocular hypertension.

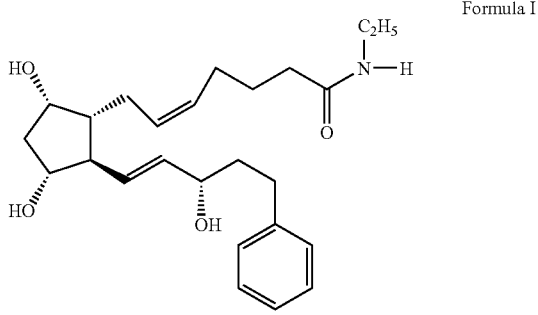

Formula I

Benzalkonium chloride (BAK) is a preservative used in many commercial ophthalmic products to prevent microbial contamination in multi-use products. The commercial eye drops (Bimatoprost, Allergan, Inc., Irvine, Calif.) contain 0.03% bimatoprost and 0.005% BAK. Although no other prostamides are currently marketed for the treatment of glaucoma, several prostaglandin analogs are commercially available which use BAK as a preservative. These include latanoprost (Xalatan), travoprost (Travatan), and unoprostone isopropyl (Rescula), which require significantly more BAK, from 150-200 ppm, to meet antimicrobial effectiveness tests in the United States and Europe.

U.S. Pat. No. 6,596,765 B2 discloses a composition comprising 0.005% or 0.0005% latanoprost and 0.2 mg/mL BAK.

U.S. Pat. No. 6,646,001 B2 discloses compositions comprising 0.03% bimatoprost and 0.01% BAK or "0.01%+5% excess" BAK.

BRIEF DESCRIPTION OF THE DRAWING FIGURES

DETAILED DESCRIPTION OF THE INVENTION

Figure 1:
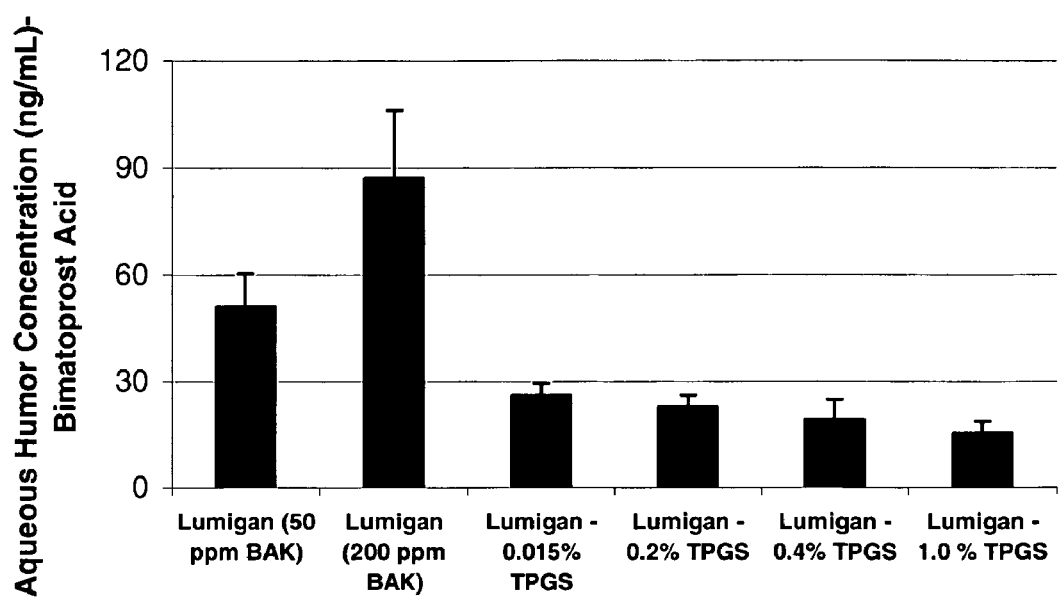
FIG. 1 is a plot showing the aqueous humor concentration of the parent acid of bimatoprost after topical administration of several formulations.

A composition comprising from 0.005% to 0.02% bimatoprost by weight and from 100 ppm to 250 ppm benzalkonium chloride, wherein said composition is an aqueous liquid which is formulated for ophthalmic administration is disclosed herein.

A method which is useful in treating glaucoma or ocular hypertension related thereto is also disclosed herein.

An aqueous liquid which is formulated for ophthalmic administration is formulated such that it can be administered topically to the eye. The comfort should be maximized as much as possible, although sometimes formulation considerations (e.g. drug stability) may necessitate less than optimal comfort.

In certain compositions the concentration of bimatoprost is from 0.01% to 0.02%. In other compositions the concentration of bimatoprost is from 0.015% to 0.02%.

In certain compositions the concentration of BAK is from 150 ppm to 200 ppm. In other compositions the concentration of BAK is from 150 ppm to 200 ppm. In other compositions the concentration of BAK is from 150 ppm to 250 ppm.

In ophthalmic compositions, a chelating agent may be used to enhance preservative effectiveness. Suitable chelating agents are those known in the art, and, while not intending to be limiting, edetate salts (EDTA) are useful chelating agents.

In certain compositions, concentration of EDTA is at least 0.001%. In other compositions, the concentration of EDTA is at least 0.01%. In other compositions the concentration of EDTA is 0.15% or less. In other compositions the concentration of EDTA is 0.1% or less. In other compositions the concentration of EDTA is 0.05% or less.

Certain compositions comprise from 150 to 250 ppm BAK and an effective amount of EDTA.

As is known in the art, buffers are commonly used to adjust the pH to a desirable range for ophthalmic use. Generally, a pH of around 6-8 is desired, and in certain compositions a pH of 7.4 is desired. Many buffers including salts of inorganic acids such as phosphate, borate, and sulfate are known.

Another commonly used excipient in ophthalmic compositions is a viscosity-enhancing, or a thickening agent. Thickening agents are used for a variety of reasons, ranging from improving the form of the formulation for convenient administration to improving the contact with the eye to improve bioavailability. The viscosity-enhancing agent may comprise a polymer containing hydrophilic groups such as monosaccharides, polysaccharides, ethylene oxide groups, hydroxyl groups, carboxylic acids or other charged functional groups. While not intending to limit the scope of the invention, some examples of useful viscosity-enhancing agents are sodium carboxymethylcellulose, hydroxypropylmethylcellulose, povidone, polyvinyl alcohol, and polyethylene glycol.

In ophthalmic solutions, tonicity agents often are used to adjust the composition of the formulation to the desired isotonic range. Tonicity agents are well known in the art and some examples include glycerin, mannitol, sorbitol, sodium chloride, and other electrolytes.

One composition has a pH of 7.4 and consists essentially of 0.015% bimatoprost, 200 ppm benzalkonium chloride, from 0 to 0.03% EDTA, a phosphate buffer, NaCl, and water.

Another composition has a pH of 7.4 and comprises 0.02% bimatoprost, 200 ppm benzalkonium chloride, from 0 to 0.03% EDTA, a phosphate buffer, NaCl, and water.

Another composition has a pH of 7.4 and consists of 0.01% bimatoprost, 200 ppm benzalkonium chloride, from 0 to 0.03% EDTA, a phosphate buffer, NaCl, and water.

The best mode of making and using the present invention are described in the following examples. These examples are given only to provide direction and guidance in how to make and use the invention, and are not intended to limit the scope of the invention in any way.

One embodiment comprises 0.01% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment comprises 0.015% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment comprises 0.015% Bimatoprost, 0.02% Benzalkonium Chloride, 0.268% Sodium Phosphate Dibasic, Heptahydrate, 0.014% Citric Acid, Monohydrate, 0.81% Sodium Chloride, 0.03%, EDTA, and water, wherein the pH is 7.3.

Another embodiment comprises 0.02% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment consists essentially of 0.01% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment consists essentially of 0.015% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment consists essentially of 0.015% Bimatoprost, 0.02% Benzalkonium Chloride, 0.268% Sodium Phosphate Dibasic, Heptahydrate, 0.014% Citric Acid, Monohydrate, 0.81% Sodium Chloride, 0.03%, EDTA, and water, wherein the pH is 7.3.

Another embodiment consists essentially of 0.02% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment consists of 0.01% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment consists of 0.015% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment consists of 0.015% Bimatoprost, 0.02% Benzalkonium Chloride, 0.268% Sodium Phosphate Dibasic, Heptahydrate, 0.014% Citric Acid, Monohydrate, 0.81% Sodium Chloride, 0.03%, EDTA, and water, wherein the pH is 7.3.

Another embodiment consists of 0.02% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

EXAMPLE 1

Formulations containing 0.268% sodium phosphate dibasic heptahydrate, 0.014% citric acid, 0.83% sodium chloride, with the pH adjusted to 7.3 in qs water, and the amounts of bimatoprost, BAK, and EDTA listed in Table 1 below were prepared by conventional methods well known in the art.

TABLE 1

| Formulation |
| --- |
| 1. 0.03% Bimatoprost (50 ppm BAK) Control |
| 2. 0.03% Bimatoprost - 200 ppm BAK |
| 3. 0.03% Bimatoprost - 0.015% TPGS (no preservative) |
| 4. 0.03% Bimatoprost - 0.2% TPGS (no preservative) |

TABLE 1-continued

| Formulation |
| --- |
| 5. 0.03% Bimatoprost - 0.4% TPGS (no preservative) |
| 6. 0.03% Bimatoprost - 1.0% TPGS (no preservative) |

EXAMPLE 2

Studies were carried out to determine the effect of benzalkonium chloride (BAK) and d-alpha tocopheryl polyethylene glycol 1000 succinate (TPGS) on ocular absorption of bimatoprost in vivo. For the in vivo study, eighteen female rabbits were given a single 28 µL eyedrop bilaterally and aqueous humor samples were collected (n=3 animals with 6 eyes per formulation) at 60 min postdose. Two rabbits (4 eyes) remained untreated to serve as pre-dose bioanalytical controls. Bimatoprost and its parent carboxylic acid extracted from aqueous humor and in vitro samples were analyzed by a liquid chromatography tandem mass spectrometry (LC-MS/MS) method with a quantitation range of 0.25-60 ng/mL.

Due to extensive metabolism of bimatoprost in rabbit eyes, its parent acid was used as a surrogate for determining ocular absorption of bimatoprost. Concentration of the acid in rabbit aqueous humor following single dose of 6 different bimatoprost formulations are summarized in FIG. 1 and Table 2 below.

TABLE 2

| Formulation | Aqueous Humor[a] (ng/mL) |
| --- | --- |
| 1. 0.03% Bimatoprost (50 ppm BAK) Control | 51.0 ± 9.4 |
| 2. 0.03% Bimatoprost - 200 ppm BAK | 87.2 ± 19.0* |
| 3. 0.03% Bimatoprost - 0.015% TPGS (no preservative) | 26.1 ± 3.3* |
| 4. 0.03% Bimatoprost - 0.2% TPGS (no preservative) | 22.9 ± 3.2* |
| 5. 0.03% Bimatoprost - 0.4% TPGS (no preservative) | 19.3 ± 5.6* |
| 6. 0.03% Bimatoprost - 1.0% TPGS (no preservative) | 15.4 ± 3.3* |

[a]Mean ± SD. Per formulation, N = 3 rabbits (6 eyes).
*Statistically different ($p < 0.05$) compared to 0.03% Bimatoprost Test formulations containing 0.015%, 0.2%, 0.4% and 1.0% TPGS resulted in a lower aqueous humor carboxylic acid concentration compared to Bimatoprost by 52%, 59%, 62% and 72%, respectively. In contrast, 0.03% Bimatoprost containing 200 ppm BAK resulted in 57% higher aqueous humor AGN 191522 concentration compared to Bimatoprost (50 ppm BAK).

While not intending to limit the scope of the invention in any way, or be bound by theory, compared to the Bimatoprost control, formulations containing TPGS resulted in decrease bimatoprost permeability. In contrast, formulations with higher BAK resulted in higher permeability.

EXAMPLE 3

Formulations containing 0.268% sodium phosphate dibasic heptahydrate, 0.014% citric acid, 0.83% sodium chloride, with the pH adjusted to 7.3 in qs water, and the amounts of bimatoprost, BAK, and EDTA listed in Table 3 below were prepared by conventional methods well known in the art.

TABLE 3

Formulation

A. 0.03% Bimatoprost (50 ppm BAK) - Control
B. 0.015% Bimatoprost (50 ppm BAK)
C. 0.015% Bimatoprost (50 ppm BAK) 0.03% EDTA
D. 0.015% Bimatoprost (200 ppm BAK)
E. 0.015% Bimatoprost (200 ppm BAK) 0.03% EDTA
F. 0.015% Bimatoprost (50 ppm BAK) 0.015% EDTA
G. 0.015% Bimatoprost (200 ppm BAK) 0.015% EDTA
H. 0.015% Bimatoprost (125 ppm BAK)
I. 0.015% Bimatoprost (125 ppm BAK) 0.03% EDTA
J. 0.015% Bimatoprost (125 ppm BAK) 0.015% EDTA
K. 0.015% Bimatoprost (150 ppm BAK)
L. 0.015% Bimatoprost (150 ppm BAK) 0.1% EDTA
M. 0.015% Bimatoprost
N. 0.03% Bimatoprost

EXAMPLE 4

The effect of benzalkonium chloride (BAK) and ethylenediaminetetraacetic acid (EDTA) on bimatoprost permeability across primary culture of rabbit corneal epithelial cell layers (RCECL). Corneal epithelial cells were harvested from New Zealand White rabbits and cultured on Transwell™ filters until confluency (Day 5). For the transport experiment, cells were first equilibrated in transport buffer for 1 hour at 37° C. Dosing solution containing 0.015% or 0.03% bimatoprost with varying concentrations of BAK and EDTA was then applied to the apical compartment of the Transwell™ (2 cultures; n=3-4 per culture) and the cells were incubated at 37° C. At 30, 60, 90 and 120 minutes postdose, 200 µL samples were taken from the basolateral chamber for apical to basolateral (AB) transport. The samples were analyzed by a liquid chromatography tandem mass spectrometry (LC-MS/MS) method with quantitation range of 1-600 ng/mL.

Figure 2:
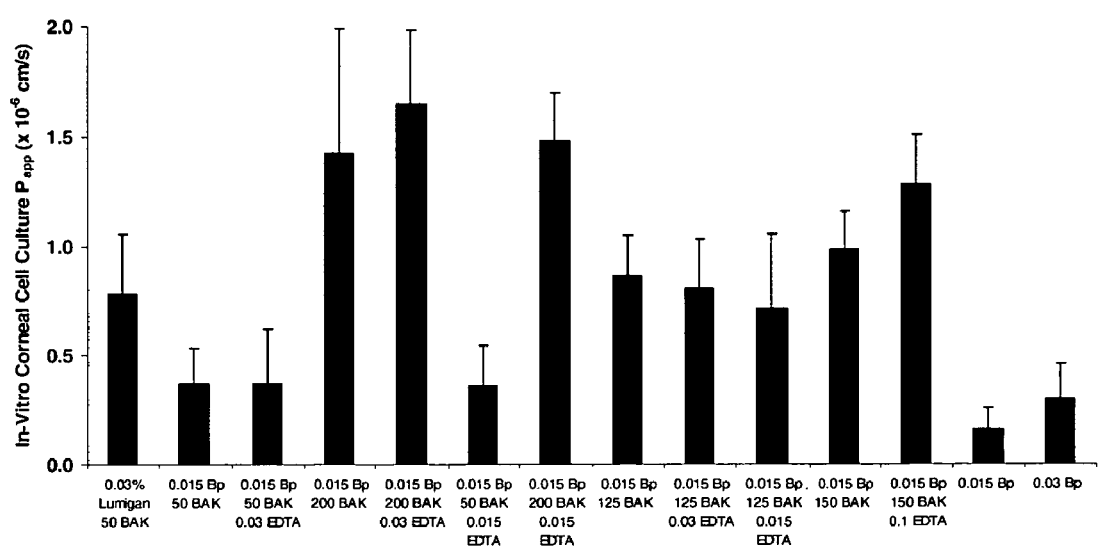
FIG. 2 is a plot showing the membrane permeability of bimatoprost in several different formulations.

The results are presented in FIG. 2.

EXAMPLE 5

A drop of formulation J is administered once daily topically to the eye of a person suffering from glaucoma. After a few hours, intraocular pressure drops more and less hyperemia is observed than would be observed for formulation A. Lowered intraocular pressure persists for as long as the treatment continues.

What is claimed is:

1. A composition having a pH of about 7.3 which consists essentially of about 0.01% bimatoprost, about 200 ppm benzalkonium chloride, a phosphate buffer, NaCl, and water, wherein said composition is an aqueous liquid which is formulated for ophthalmic administration.

2. A composition having a pH of about 7.3 which comprises about 0.01% bimatoprost, about 200 ppm benzalkonium chloride, citric acid monohydrate, a phosphate buffer, and NaCl wherein said composition is an aqueous liquid which is formulated for ophthalmic administration.

3. A composition having a pH of about 7.3 which comprises about 0.01% bimatoprost, 200 ppm benzalkonium chloride, about 0.014 citric acid monohydrate, a phosphate buffer, NaCl, and water wherein said composition is an aqueous liquid which is formulated for ophthalmic administration.

* * * * *